(12) United States Patent
Chwalisz et al.

(10) Patent No.: US 8,193,252 B1
(45) Date of Patent: Jun. 5, 2012

(54) MESOPROGESTINS (PROGESTERONE RECEPTOR MODULATORS) FOR THE TREATMENT AND PREVENTION OF BENIGN HORMONE DEPENDENT GYNECOLOGICAL DISORDERS

(75) Inventors: Kristof Chwalisz, Hawthorn Woods, IL (US); Walter Elger, Berlin (DE); Gerd Shubert, Jena (DE)

(73) Assignee: Bayer Pharma AG, Berlin (DE)

( * ) Notice: Subject to any disclaimer, the term of this patent is extended or adjusted under 35 U.S.C. 154(b) by 1449 days.

(21) Appl. No.: 10/450,029

(22) PCT Filed: Aug. 31, 2000

(86) PCT No.: PCT/US00/23770
§ 371 (c)(1),
(2), (4) Date: Dec. 16, 2003

(87) PCT Pub. No.: WO01/15679
PCT Pub. Date: Mar. 8, 2001

Related U.S. Application Data

(60) Provisional application No. 60/266,323, filed on Aug. 31, 1999.

(51) Int. Cl.
*A61K 31/56* (2006.01)
(52) U.S. Cl. ........ 514/899; 514/177; 514/178; 514/179; 514/843
(58) Field of Classification Search .................. 514/177, 514/178, 179
See application file for complete search history.

(56) References Cited

U.S. PATENT DOCUMENTS

| | | | |
|---|---|---|---|
| 4,670,426 A | 6/1987 | Zor et al. | |
| 5,469,836 A | 11/1995 | Greenall | |
| 5,576,310 A | 11/1996 | Schubert et al. | |
| 5,693,628 A * | 12/1997 | Schubert et al. | 514/179 |
| 5,696,133 A | 12/1997 | Hamann et al. | |
| 6,451,780 B1 * | 9/2002 | Chwalisz et al. | 514/179 |

FOREIGN PATENT DOCUMENTS

| | | |
|---|---|---|
| DE | 4332283 | 4/1995 |
| DE | 19809845 | 9/1999 |
| WO | WO 93/21926 | 11/1993 |
| WO | WO 9520972 | 8/1995 |
| WO | WO 9727863 | 8/1997 |
| WO | WO 9805679 | 2/1998 |
| WO | WO 0042031 | 7/2000 |
| WO | WO 0066590 | 11/2000 |

OTHER PUBLICATIONS

Enotes: Encylopedia of Medicince Dysfunctional Uterine Bleeding May 31, 2006 pp. 1-5.*
Martha et al. (Fertility and Sterility 1999, 71(4), supplement 1, p. 9S).*
Lessey (Fertility and Sterility Jun. 2000, 73(6), 1089-1096).*
Schneider et al. (Abstract: Exp. Clin. Endocrinol. Diabetes 1998, 106, suppl. 1, s52).*
MedlinePLus medical encyclopedia: uterine fibroids [online] retrieved from the internet on Oct. 23, 2007; retrieved from http://www.nlm.nih.gov/medlineplus/ency/article/000914.htm; May 15, 2007; 3 pages.*

* cited by examiner

*Primary Examiner* — Ernst Arnold
(74) *Attorney, Agent, or Firm* — Millen, White, Zelano & Branigan, P.C.

(57) ABSTRACT

This present invention disclosed the use of mesoprogestins, a new class of progesterone receptor modulators (PRMs), for the treatment and prevention of benign hormone dependent gynecological disorders: a) for the treatment of gynecological disorder such as endometriosis, uterine fibroids, postoperative peritoneal adhesions, dysfunctional bleeding (metrorrhagia, menorrhagia) and dysmenorrhea; b) for the prevention of gynecological disorders such as postoperative, peritoneal adhesions, dysfunctional uterine bleeding (metrorrhagia, menorrhagia) and dysmenorrhea; and c) a method of treatment and prevention of the above mentioned disorders in a female, preferably in a human female, in need of treatment or prevention of one or more of these disorders, with an effective amount of a mesoprogestin. Mesoprogestins are defined as compounds possessing both agonistic and antagonistic activities at the progesterone receptor (PR) in vivo. They stabilize the function of PR at an intermediate level of agonistic and antagonistic. Corresponding functional states cannot be achieved with progestins or antiprogestins. The daily dose of mesoprogestin is 0.5 to 100 mg, preferably 5.0 to 50 mg and most preferably 10 to 25 mg. J867, J912, J956 and J1042 are the mesoprogestins preferred according to the invention.

22 Claims, 2 Drawing Sheets

Progesterone-like (above, Fig. 1A) and progesterone antagonistic (below, Fig. 1B) effects of PR-modulators in the uterus of estrogen primed immature rabbits (McPhail test)

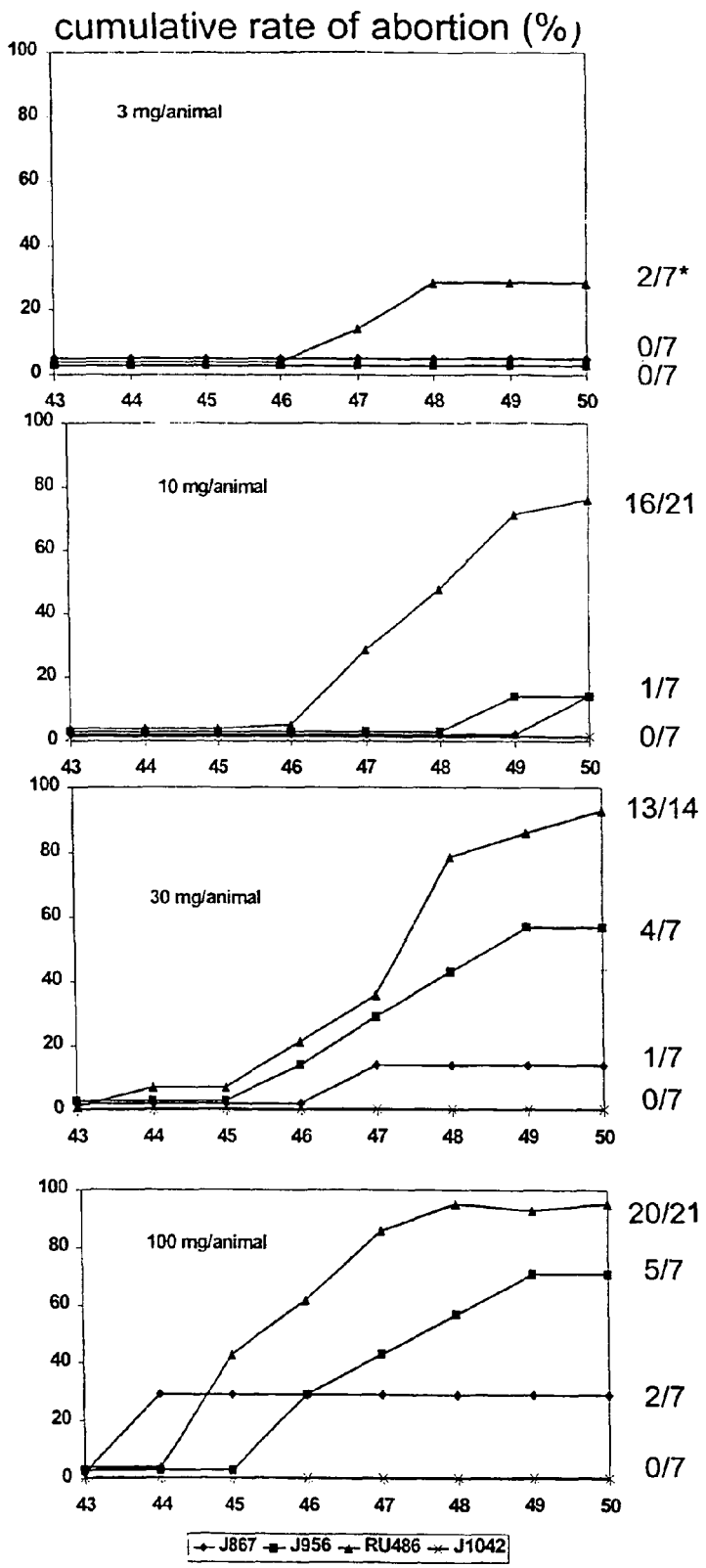
Figure 2: Cumulative rate of abortion until day 50 in guinea pigs treatment on days 43 and 44 of pregnancy by s.c. injection. (#/#) = rate of abortion

MESOPROGESTINS (PROGESTERONE RECEPTOR MODULATORS) FOR THE TREATMENT AND PREVENTION OF BENIGN HORMONE DEPENDENT GYNECOLOGICAL DISORDERS

This application is a 35 U.S.C. §371 National phase filing from International Application No. PCT/US00/23770, filed Aug. 31, 2000, which International application claims priority to U.S. Provisional Application No. 60/266,323, filed Aug. 31, 1999.

This invention relates to the treatment and prevention of major benign hormone dependent gynecological disorders, including the proliferative conditions such as endometriosis, uterine fibroids and postoperative peritoneal adhesions, as well as menstrual syndromes, dysfunctional bleeding (metrorrhagia, menorrhagia) and dysmenorrhea.

Classically, these disorders are treated with medium or high dose progestins. This treatment, which efficacy is sometimes variable, is, however, associated with undesirable side-effects, including metabolic changes (increase in LDL and decrease in HDL concentrations), effects on mood, and breakthrough bleeding.

More recently, competitive progesterone receptor antagonist (antiprogestins), including onapristone, RU 486 (mifepristone), have been proposed as a novel approach for the treatment of endometriosis and dysmenorrhea (EP 0 266 303 B1), uterine fibroids [Yen SSC (1993) Use of antiprogestins in the management of endometriosis and leiomyomata. In Donaldson, M:s., Dorflinger (eds). Clinical application of Mifepristone (RU 486) and other antiprogestins. National Academy Press, Washington, D.C., pp. 189-209; Kettel L. M., Murphy A. A., Morales A. J. et al., (1996) Treatment of endometriosis with the antiprogesterone mifepristone (RU 486). Fertil Steril 65: 23-28], and uterine bleeding disorders (WO 96/23503).

A potential drawback of antiprogestins is that their misuse for abortion cannot be ruled out completely.

Endometriosis

Endometriosis is a chronic disease characterized by ectopic growth of the endometrium, i.e. outside of the uterine cavity. The exact overall incidence of endometriosis is not known despite efforts to estimate how frequently it occurs and to fix the rates of occurrence in specific clinical situations (6, 8, 9, 11). The figures range from 5% to 55%. The disease is characterized by histologically benign proliferation and function of the endometrial glands and stroma outside of their physiological location.

The ovary is the most common site of endometriosis (50-60%). Other commonly affected areas are: the uterosacral ligaments, cul-de-sac, uterovesical peritoneum, retrovaginal septum, and uterine ligaments. The endometriotic lesions may also be found on the organs, including the sigmoid colon, appendix, rectum, bladder, etc.

Endometriosis must be viewed as a disease of varying severity which frequently occurs in association with infertility and with significant dysfunction of pelvic pain. The clinical symptoms of endometriosis include dysmenorrhea, dyspareunia, chronic pelvic pain, dysuria, various genitourinary symptoms secondary to urethral obstruction and/or bladder invasion, painful defecation, rectal pressure, defecation urgency and bowel obstruction, bleeding abnormalities, including menorrhagia or metrorrhagia, infertility, primary or secondary, recurrent spontaneous abortions, The major clinical symptoms are primary or acquired dysmenorrhea, dyspareunia and pelvic pain, especially in the ovulatory period.

The basic goals of medical therapy of endometriosis are to produce atrophy of endometriotic lesions and induce an acyclic hormone environment using GnRH-agonists/-antagonists or continuous progestin treatment. Generally, these treatments produce a hypoestrogenic environment leading to the improvement of the disease.

The most frequently used progestins for medical therapy of endometriosis are danazol and gestrinone. Danazol is isoxazole derivative of 17-ethinyl testosterone with pronounced androgenic partial activity. Gestrinone is a derivative of 19-nortestosterone with potent gestagenic and androgenic properties. It has some advantages over danazol like less frequent administration, better contraceptive protection, and less influence on lipid metabolism. Danazol, the most widely used progestin is widely believed to act by suppressing cyclical gonadotrophin secretion, but there is growing evidence that this compound displays a multiple mechanism of action, including a direct inhibition of ectopic endometrial tissue. Treatment with danazol is associated with pronounced side effects. As many as 85% of women treated with danazol have side effects (67,68) such as: androgenic and anabolic changes (acne and oily skin, deepening of the voice, weight increase, increased LDL and decreased HDL concentrations, other side effects like edema, hypertension due to the glucocorticoid and mineralocorticoid partial activity of danazol, and intermenstrual bleeding.

Pituitary suppression can be achieved with GnRH-agonists and GnRH-antagonists. Different GnRH-agonists are currently used in treating endometriosis. This therapeutic regimen induces a profound hypoestrogenic, acyclic environment without exerting steroidal side effects. GnRH-analogs are effective in the treatment of endometriosis. Subjective and objective effects of this treatment are comparable to or even better than those of danazol (72-77). Signs and symptoms due to estrogen deprivation (hot flushes, psychic alternations, headache, tiredness, etc.) are the major side effects. In addition, GnRH-analogs therapy can induce osteoporosis (76,77). The possibility of accelerated bone loss during GnRH-analogs induced ovarian suppression is the major concern of an otherwise effective therapy for endometriosis.

In the meantime different add back regimes have been contemplated to substitute the estrogen suppression during GnRH-treatment by a selective estrogen receptor modulateo (SERM) like raloxifene (SAG: WO 97/27863; Eli Lilly).

Menorrhagia

Menorrhagia is defined as menstrual bleeding>80 ml per period, a syndrome of unknown origin, is one of the most common problems in gynecology. 60% of women refereed with menorrhagia have a hysterectomy within five years. The current medical treatment remains still unsatisfactory. The most commonly prescribed drug in Europe for an acute treatment during menstruation is norethisterone (~40%), followed by the nonsteroidal antiinflammatory drug (NSAID) mefenamic acid (~30%) and the antifibrinolytic drug tranexamic acid (5%) (Intercontinental Medical Statistics 1994). The last compound seems to be most effective in women with ovulatory menorrhagia (blood loss reduction by 45%) after acute administration during bleeding. Recently, the levonorgestrel intrauterine system (Mirena) has been introduced for the prevention of menorrhagia. A recent study has shown that both the levonorgestrel intrauterine system (Mirena) and oral norethisterone administered at a dose of 5 mg three times daily from day 5 to 26 of the cycle for three cycles provided an effective treatment (prevention) of menorrhagia in term of reducing to within normal limits. However, both treatment regimens were associated with high level of intermenstrual bleeding (50% of women treated with Mirena and 36% receiving norethisterone) (Irvine et al., 1998).

Dysmenorrhea

Dysmenorrhea is caused by painful uterine contractions. Women with dysmenorrhea have higher intrauterine resting and peak pressures when compared to normal controls. The exact mechanism of pain in dysmenorrhea is still unclear. Dysmenorrhea is most likely caused by increased uterine contractions and basal tone as well as a vasoconstriction of the spiral arteries during menstruation (Pickels et al., 1965; Csapo et al., 1977). Prevention of both uterine contractions and vasoconstriction of uterine vessels should, therefore, provide a relief of perimenstrual pain. Dysmenorrhea can be classified as primary or secondary dysmenorrhea (Dawood 1985; 1990). In primary dysmenorrhea there are painful menstrual cramps but no visible pelvic pathology to account for them. In secondary dysmenorrhea, however, there is visible pelvic pathology (e.g. endometriosis) which causes the painful menstrual cramps.

Primary dysmenorrhea is one of the most frequent gynecologic complains and affects as many as 50% of postpubercent females (Dawood 1985; 1990). With the availability of oral contraceptives and NSAIDs, both of which relieve primary dysmenorrhea effectively, the apparent prevalence rate may in fact be somewhat lower. Ten percent of women with primary dysmenorrhea have severe pain to render them incapacitated for 1 to 3 days each month, a situation leading to significant absenteeism (Svennerud, 1959) and consequent economic loss (Dawood 1985). Dysmenorrhea is therefore a significant medical and economic problem and better (simpler, safer) treatment can reduce the burden of disease to women and society.

Primary dysmenorrhea appears to be a single disease entity while secondary dysmenorrhea can be caused by a variety of disorders, including endometriosis and uterine fibroids. In general the treatment for primary dysmenorrhea is medication, whereas secondary dysmenorrhea usually requires surgical therapy for the underlying pathology (exceptions: secondary dysmenorrhea caused by the presence of an IUDs and endometriosis). Primary dysmenorrhea is most prevalent among young women in their teens or early twenties, declining again after the age of 30 (Widholm, 1979). Primary dysmenorrhea can be diagnosed on the basis of medical history and clinical features, physical examination and transvaginal ultrasound scan to exclude uterine abnormalities (Dawood, 1990).

Combined OCs and NSAIDs are widely used for prevention or treatment of perimenstrual pain. Both medications are effective in about 80-90% women with primary dysmenorrhea [Dawood, 1990]. However, 10-20% women with severe primary dysmenorrhea are resistant to any treatment. In Germany ibuprofen (Urem$^R$, Gynofug$^R$) is the most popular NSAID in dysmenorrhea. However, not all women/girls with primary dysmenorrhoea wish to take OCs or can tolerate NSAIDs treatment. This is the case particularly with girls between 13-16. Alternative medical therapy employs tocolytic drugs such as calcium channel blockers (Sandah et al., 1979) or betamimetics (Dawood, 1990). These act by suppressing uterine contractions but have not been found to be acceptable to patients, gynecologists and general physicians on a larger scale. The same applies to the progesterone releasing IUS. Transcutaneous electrical nerve stimulation (TENS) has been found to be only 30% effective in women with severe dysmenorrhea (Lundberg et al., 1985).

Therefore better tolerated and/or more accepted strategies to treat the aforementioned conditions are highly desirable.

This invention discloses the use of mesoprogestins, a new class of progesterone receptor modulators (PRMs), for the treatment and prevention of benign hormone dependent gynecological disorders.

One aspect of the invention is the use of mesoprogestins for the manufacture of medicaments for the treatment of gynecological disorder such as endometriosis, uterine fibroids, postoperative peritoneal adhesions, dysfunctional bleeding (metrorrhagia, menorrhagia) and dysmenorrhea.

Another aspect of the invention is the use of mesoprogestins for the manufacture of medicaments for the prevention of gynecological disorders such as postoperative, peritoneal adhesions, dysfunctional uterine bleeding (metrorrhagia, menorrhagia) and dysmenorrhea.

Another aspect of the instant invention refers to the treatment and prevention of the above mentioned disorders in a female, preferably in a human female, in need of treatment or prevention of one or more of these disorders, with an effective amount of a mesoprogestin.

Yet another aspect of the invention is the use of a daily dose of 0.5 to 100 mg mesoprogestin for treatment of the mentioned conditions.

More preferred is a daily dose of 5.0 to 50 mg mesoprogestin and most preferred is a daily dose of 10 to 25 mg of a mesoprogestin.

As mesoprogestins i.a. compounds disclosed in DE 43 32 283 and in DE 43 32 284 are suitable for the purposes of the invention.

As mesoprogestins are preferred the compounds J867, J912, J 900, J 914 and J956 [J 867 [4-[17β-Methoxy-17α-(methoxymethyl)-3-oxoestra-4,9-dien-11β-yl]benzaldehyd-(1E)-oxim] and J 912 [4-[17β-Hydroxy-17α-(methoxymethyl)-3-oxoestra-4,9-dien-11β-yl]benzaldehyd-(1E)-oxim] (both DE 43 32 283) and J 900 [4-[17β-Methoxy-17α-(methoxymethyl)-3-oxoestra-4,9-dien-11β-yl]benzaldehyd-(1E)-[O-(ethoxy)carbonyl]oxim], J 914 [4-[17β-Methoxy-17α-(methoxymethyl)-3-oxoestra-4,9-dien-11β-yl]benzaldehyd-(1E)-(O-acetyl)oxim] and J 956 [4-[17β-Methoxy-17α-(methoxymethyl)-3-oxoestra-4,9-dien-11β-yl]benzaldehyd-(1E)-[O-(ethylamino)carbonyl]oxim] (all DE 43 32 284) and J1042 [4-[17β-Methoxy-17α-(methoxymethyl)-3-oxoestra-4,9-dien-11β-yl]benzaldehyd-(1E)-[O-(ethylthio)carbonyl] oxim (German Patent Application 198 09 845.6)] for the treatment and prevention of the above mentioned conditions as well as mesoprogestin component in the pharmaceutical compositions and combinations mentioned thereafter which can also be used for treatment and prevention of the above mentioned conditions.

J 867 is described in DE 43 32 283 and J 900 and 914 are described in DE 43 32 284 as well as in corresponding patent applications as compounds having strong antiprogestagenic and compared to RU 486 having markedly reduced antiglucocorticoid activity. Moreover these compounds are mentioned to have (indirect) antiestrogenic properties reflected by reduced uterine weights in cyclic guinea pigs.

These effects should promise the exertion of a particularly favorable influence on pathologically modified tissues in which estrogens stimulate growth (endometriotic focuses, myomas, etc.) but it is not said expressis verbis that just the described compounds should be suitable in these indications. Also, the mentioned applications are silent about any active dose to be used to treat the mentioned conditions.

A progestagenic activity of the compounds disclosed is not mentioned in these applications at all.

According to the invention mesoprogestins are defined as compounds possessing both agonistic and antagonistic activities at the progesterone receptor (PR) in vivo. As progestins and antiprogestins, mesoprogestins show high binding affinity to PR. However, mesoprogestins exhibit different pharmacodynamic properties compared to either progestins or antiprogestins. The presence of progesterone agonistic activity in mesoprogestins measured in commonly used biological tests in vivo represents the key property of this novel class of PRMs. This activity remains, however, below that of progesterone in the plateau of the dose response curve. Mesoprogestins fail to maintain pregnancy in ovariectomized pregnant rodents as mice and rats.

In the classical bioassay, the McPhail test, assessing progestagenic and antiprogestagenic effects in rabbits (Selye H., Textbook of Endocrinology, 1947, pp. 345-346), progesterone produces a maximum McPhail score of 4 (by definition). Treatment with a mesoprogestin in the absence of progesterone leads, however, to a McPhail score which is higher than that under any dose of RU 486, i.e. above 0.5-1.0, preferentially 2.0-3.0, but to distinctly lower score than 4 at the plateau of the dose response curve at the clinically relevant doses for the claimed indications (i.e. 0.01 mg-30 mg/rabbit).

The capacity of mesoprogestins to antagonize progesterone function is also tested in the McPhail test using a progesterone dose which induces a McPhail score ranging between 3 and 4. A mesoprogestin inhibits the effect of progesterone to a significant degree, but the maximum inhibition is below that which is inducible with RU 486 or other pure antiprogestins (e.g. onapristone).

The mesoprogestins stabilize, therefore, the function of PR at an intermediate activity level providing the rationale for the novel clinical applications in gynecological therapy. Corresponding functional states cannot be achieved with progestins or antiprogestins.

Pharmacological Results Demonstrating the Utility of the Mesoprogestines in the Claimed Indications The PR antagonistic and agonistic properties of mesoprogestins were assessed in estrogen-primed rabbits in the McPhail test according to Selye (Textbook of Endocrinology, 1947, pp. 345-346).

A) Assessment of PR Agonistic Properties of Mesoprogestins in Rabbits (FIG. 1A)

The progestagenic activity of J867, J956, J1042 and RU 486 (dose range: 0.003-100 mg/rabbit) was evaluated in estradiol-primed juvenile rabbits after 4 days of subcutaneous (s.c.) treatment in the absence of progesterone). The progestagenic effect of the mesoprogestins was observed at doses equal to or higher that 0.03 mg/rabbit. Progesterone induced endometrial transformation at doses equal to or higher that 0.1 mg reaching a maximum effect at 1 mg/rabbit (approximately McPhail score 4). Neither mesoprogestin tested (J1042, J867, J956) reached the maximum effect of progesterone. J956 showed a biphasic response in this test with a maximum effect of McPhail score 1.5 at 0.3-1 mg/rabbit.

B) Assessment of PR Antagonistic Properties of Mesoprogestins in Rabbits (FIG. 1B)

Similarly, the antiprogestagenic activity of J867, J956, J1042 and RU 486 (dose range: 0.001-100 mg/rabbit) was evaluated in estradiol-primed juvenile rabbits after 4 days of subcutaneous (s.c.) treatment in the presence of progesterone (1 mg/rabbit s.c.). The first antiprogestagenic effect of the mesoprogestins and RU 486 was observed with a dose of 0.3-1 mg mg/rabbit (McPhail index 0=no transformation; 4=complete transformation). The antiprogestagenic activity of mesoprogestins at higher clinically relevant doses doses (i.e. 3-30 mg/rabbit) was lower that that of RU 486.

In the guinea pig model which allows a good prediction of the effects in humans with respect to the abortifacient activity (Elger W, Beier S., Chwalisz K, Fähnrich M, Hasan S H, Henderson D, Neef G, Rohde R (1986): Studies on the mechanism of action of progesterone antagonists. J Steroid Biochem 25: 835-845) the mesoprogestins J 867, J 912, J 956, J 1042 lead up to 100 mg/kg/day to a maximal abortion rate of 20%.

The presence of agonistic activity at the progesterone receptor is beneficial with respect to endometrial protection, i.e. prevention of endometrial hyperplasia due to unopposed estrogen effect on endometrium. Signs of endometrial hyperstimulation were previously described after prolonged treatment of endometriosis with RU 486 (Murphy A A, Kettel L M, Morales A J, et al., (1995) Endometrial effects of long-term, low-dose administration of RU 486, Fertil. Steril. 63: 761-766).

C) Evaluation of Abortifacient Effects
Physiological Background:

The guinea pig is considered as relevant model of human gestation and parturition (Elger W, Fähnrich M, Beier S, Quing S S, Chwalisz K (1987). Endometrial and myometrial effects of progesterone antagonists in pregnant guinea pigs. *Am J Obstet Gynecol* 157: 1065-1074; Elger W, Neef G, Beier S, Fähnrich M, Gründel M, Heermann J, Malmendier A, Laurent D, Puri C P, Singh M M, Hasan S H, Becker H (1992). Evaluation of antifertility activities of antigestagens in animal model. In: Puri C P and Van Look P F A (eds), *Current Concepts in Fertility Regulation and Reproduction*. Wiley Eastern Limited, New Delhi, pp. 303-328; Elger W, Faehnrich M, Beier S, Qing S S, Chwalisz K (1986). Mechanism of action of progesterone antagonists in pregnant guinea pigs. *Contraception* 6: 47-62; Elger W, Chwalisz K, Faehnrich M, Hasan S H, Laurent D, Beier S, Ottow E, Neef G, Garfield R E (1990). Studies on labor-conditioning and labor-inducing effects of antiprogesterones in animal model. In: Garfield R E (eds), Norwell, pp. 153-175.) The mechanism of abortion of antiprogestins in this species is the initiation of labor and finally the expulsion of the conceptus. Abortifacient effects in the rat during very early pregnancy reflect inhibitory effects on nidation rather than initiation of uterine contractions. Studies in the rat model lead to "overestimation" of the potential of antiprogestins to terminate pregnancy in humans. Conversely, in the guinea pig model, irrespective of the antiprogestin doses, there were high rates of ongoing pregnancies similar to the situation in humans (Elger et al., *Current Concepts in Fertility Regulation and Reproduction* cited above). Furthermore, in both humans and guinea pigs, there is a strong synergism between antiprogestins and prostaglandins with respect the induction of labor (see the articles cited above and Elger W, Beier S (1983). Prostaglandine and Antigestagene für den Schwangerschaftsabbruch (Prostaglandins and antigestagens for pregnancy termination). German Patent DE 3337450 12; Van Look P, Bygdeman M (1989). Antiprogestational steroids: a new dimension in human fertility regulation. *Oxford reviews of reproductive medicine* 11: 2-60).

Assessment of Labor Inducing Activity: FIG. 2.

Pregnant guinea pigs were treated on days 43 and 44 of pregnancy and observed until day 50 of gestation. For the effects of various treatments see table 1 and FIG. 2. It is typical for this model that expulsions occur with a delay of several days after treatment. It can be seen that Mesoprogestins have a much reduced abortifacient activity compared to RU486. The following ranking of abortifacient activity was found: RU486>J956>J867, J912>J1042. The differences with respect to abortifacient activity seem qualitative ones. It is not possible to overcome the low abortifacient activity of a Mesoprogestin by the use of a higher dose.

TABLE 1

Studies of relative binding activity (RBA) and $ED_{50}$ of abortifacient activity in pregnant rats and guinea pigs.

| compound | RBA (%)# | | abortifacient activity $ED_{50}$ (mg/animal/day, s.c.) | |
|---|---|---|---|---|
| | $PR^1$ | $GR^2$ | $rat^3$ | guinea $pig^4$ |
| RU 486 | 506 | 685 | 0.98* | 3.8 |
| Onapristone | 22 | 39 | 1.71* | ca 3 |
| J867 | 302 | 78 | 0.65* | >100 |
| J956 | 345 | 154 | 0.64* | 20 |
| J912 | 162 | 16 | 0.36 | >100 |
| J1042 | 164 | 42 | >10 | >>100 | by Kaufmann;
[1]progesterone = 100%,
[2]dexamethasone = 100%
[3]treatment days 5-7 of pregnancy, autopsy day 9,
[4]treatment day 43-44 of pregnancy, autopsy day 50,
*SAS, probit procedure.

Application Forms of the Mesoprogestines for the Purposes of this Invention:
  oral dose range: 0.5 mg/day-100 mg/day
  intramuscular 0.1 mg-50 mg/day
  intrauterine (IUS), intravaginal (gel, sponge)
Galenical Formulation:
  Galenical formulations can be provided conventionally, for instance as described in the basic patent applications for the compounds J867, J912, J956 (DE 43 32 283 and DE 43 32 284).
  Also, applications can be provided, as known, for transdermal (gel, patch) or intravaginal (gel, suppository) administration
Combinations of the Mesoprogestins According to the Invention with Other Pharmacologically Active Compounds:
Endometriosis and Uterine Fibroids:
  GnRH-agonists/-antagonist plus mesoprogestin sequentially (2-3 months GnRH-agonist/antagonist followed by a mesoprogestin for 3-6 months to maintain the therapeutical effect).
  Combined use of GnRH-agonist/-antagonist for 3-6 months with a mesoprogestin (add back-therapy) in order to reduce GnRH-induced side effects (hot flushes, osteoporosis).
  The GnRH-agonist/-antagonist for the aforementioned purposes is selected from the group of leuprorelin (U.S. Pat. No. 4,005,063), cetrorelix (EP 0 299 402 B1), antide WO-A-89/01944), buserelin (GB 1 523 623), ramorelix (EP 0 541 791 A), zoladex (U.S. Pat. No. 4,100,274), 2-(4-acetylaminophenyl)-4,7-dihydro-7-(2-methoxybenzyl)-3(N-methyl-N-benzylaminomethyl)-4-oxothieno[2,3-b]-pyridin-5-carbonic acid ethyl ester (WO-A 95/28405), 5-benzoyl-7-(2,6-difluorobenzyl)-4,7-dihydro-3-(N-methyl-N-benzylaminomethyl)-2-(4-propionylamidophenyl)-4-oxothieno[2,3-b]-pyridine and Ac-D-Nal-D-Cpa-D-Pal-Ser-Tyr-D-Cit-Leu-Lys(Mor)-Pro-D-Ala-$NH_2$ (WO-A 92/20711).
Dysfunctional Bleeding:
  Combination with cyclooxygenase inhibitors (e.g. mefenamic acid, aspirin)
  Combination with an antifibrinolytic agent (e.g. tranexamic acid)
Dysmenorrhea
  Combination with cyclooxygenase inhibitors (e.g. mefenamic acid, aspirin)
  Combination with NO donors (e.g. nitroglycerin)

Regimes of Application Used for the Different Indications:
endometriosis and uterine fibroids
  see above under combinations
Treatment of Dysfunctional Uterine Bleeding:
  from the onset of bleeding until the cessation of bleeding
Prevention of Dysfunctional Uterine Bleeding:
  d1 up to the end of the third month daily (duration 28 to 60 days)
Treatment of Dysmenorrhoea:
  d1 up to cessation of the symptoms
Prevention of Dysmenorrhoea:
  from 3 days up to 28 days before beginning of menstruation

EXAMPLES

1. Acute Treatment of Dysfunctional Bleeding with a Mesoprogestin

Women exhibiting menorrhagia or other form of dysfunctional bleeding are treated for 1-10 days with 5-100 mg of J867 until the cessation of treatment.

2. Prevention of Dysfunctional Bleeding with a Mesoprogestin

Women with menorrhagia or other form of dysfunctional bleeding are treated with 0.5-25 mg J867 starting on the first day of bleeding for 21-60 day.

3. Treatment of Endometriosis

Women with endometriosis are treated for 3-6 months with 5-50 mg J 867, During treatment the reduction of pelvic pain was observed 4. Sequential Treatment of Endometriosis with an LHRH Agonist and J867

Women with endometriosis are treated for 2-3 months with an LHRH agonist such as Lupron. After the cessation of LHRH-agonist therapy women are treated for the next 3-6 months with J 867 in order to avoid osteoprorosis induced by prolonged treatment with LHRH agonist. During treatment with 5-50 mg J 867 the therapeutic effects of the LHRH-agonist are maintained. Treatment with J867 does not produce estrogen deficiency, since the plasma estradiol levels are at the level of the follicular phase.

5. Treatment of Uterine Fibroids

Women with endometriosis are treated for 3-6 months with 5-50 mg J 867, During treatment the reduction of pelvic pain was observed.

The entire disclosure of all applications, patents and publications, cited above or below, and of corresponding provisional application filed as U.S. Ser. No. 09/386,141 on Aug. 31, 1999, and converted to provisional by petition of Aug. 29, 2000 is hereby incorporated by reference.

The preceding examples can be repeated with similar success by substituting the generically or specifically described reactants and/or operating conditions of this invention for those used in the preceding examples.

BRIEF DESCRIPTION OF THE DRAWINGS

FIG. 2 is graphs showing data on the assessment on cumulative rate of abortion until day 50 in guinea pigs treated on days 43 and 44 of pregnancy.

Figure 1A:
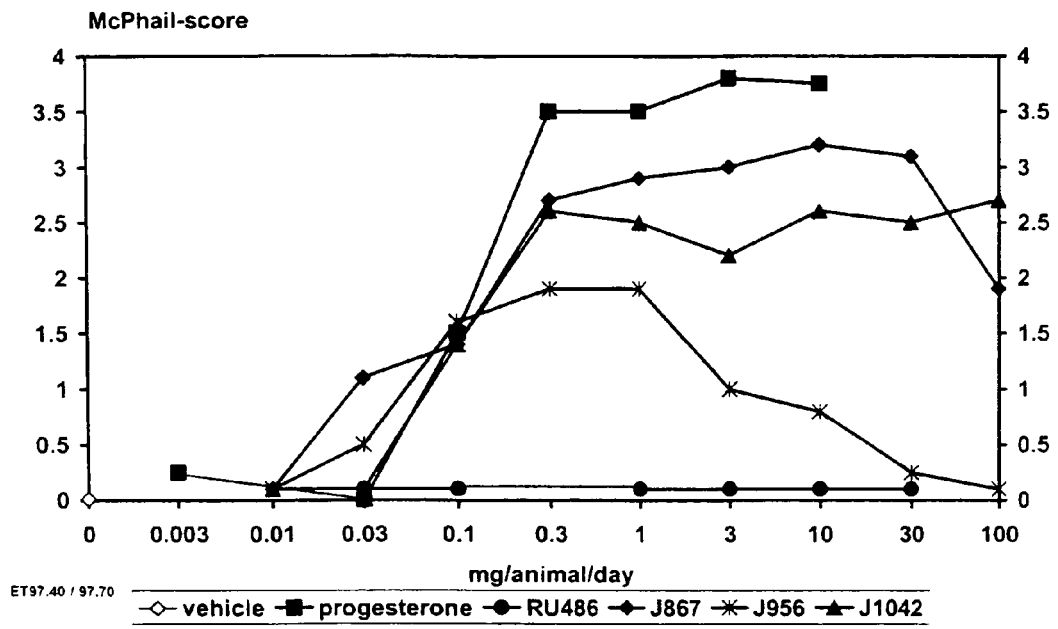
FIGS. 1A and 1B are graphs showing data on the progesterone-like (FIG. 1A) and progesterone antagonistic (FIG. 1B) effects of PR-modulators in the uterus of estrogen primed immature rabbits (McPhail test).
Figure 1B:
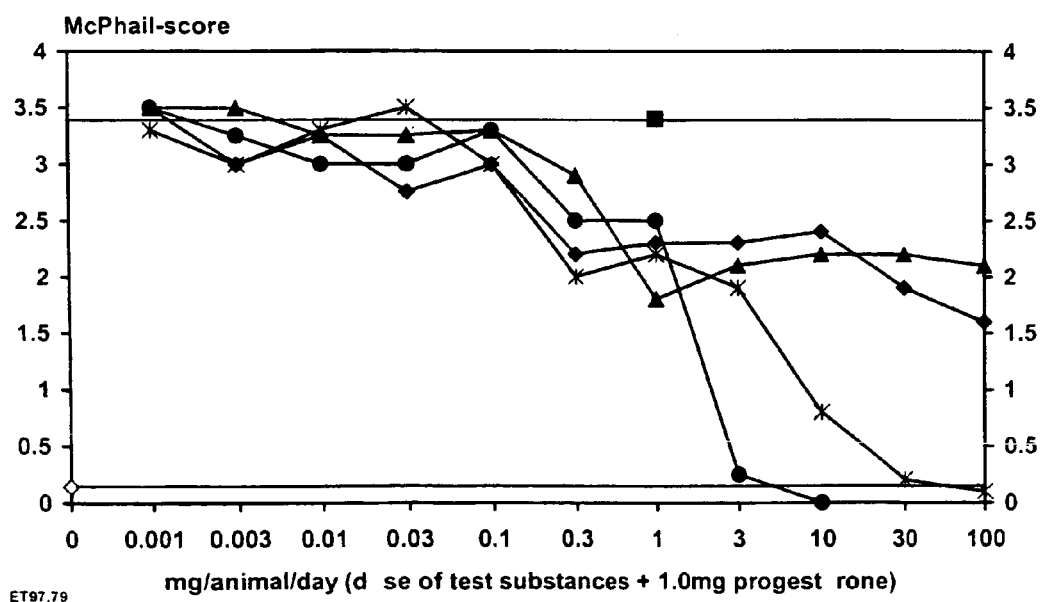

From the foregoing description, one skilled in the art can easily ascertain the essential characteristics of this invention and, without departing from the spirit and scope thereof, can make various changes and modifications of the invention to adapt it to various usages and conditions.

LITERATURE

Preston J T, Cameron I T, Adams E J, Smith S K (1995) Comparative study of tranexamic acid and norethisterone in the treatment of ovulatory menorrhagia. Br. J Obstet Gynecol 102:401-406

Bonnar J, Sheppard B I (1996) Treatment of menorrhagia during menstruation: randomised controlled trial of ethamsylate, mefenamic acid and tranexamic acid. BMJ 313: 579-582

Intercontinental Medical Statistics Ltd. London:IMS, 1994

Chwalisz K., Buhimschi I., Garfield R. E. (1996) Role of nitric oxide in obstetrics. Prenat Neonat Med 1,: 292-329.

Dawood M Y (1984) Ibuprofen and dysmenorrhea. Am J Med 77: 87

Dawood M Y (1985) Etiology and treatment of dysmenorrhoea Semin Reprod Endocrinol 3:283

Dawood M Y (1990) Dysmenorrhoea Clin Obstet Gynaecol 33:168

Dawood M Y (1985) Overall approach to managing dysmenorrhoea. In Dawood M Y, McGuire J L Demers L M, eds. Premenstrual syndrome and dysmenorrhoea. Baltimore: Urban Schwarzenberg, pp: 177

Lundberg T, Bondesson L, Lundstrom V (1985) Relief of primary dysmenorrhoea by transcutaneous electrical nerves stimulation. Acta Obstet Gynaecol Scand 64:491

Pittrof R, Lees C, Thompson C, Martin J F, Campbell S (1996) Glyceryl trinitrate patches reduce pain in women with severe dysmenorrhoea. Brit Med J 312:884

6. Williams, T, Pratt, J H: Endometriosis in 1000 consecutive celiotomies: medicine and management. Am J Obstet Gynecol 129:245 (1977)

8. Redwine D B: The distribution of endometriosis in the pelvis by age groups and fertility. Fertil Steril 47:173 (1987)

9. Houston D E: Evidence for the risk of pelvic endometriosis by age, race and socioeconomic status. Epidemiol Rev 6:167 (1984)

11. Chartman, D L, M D: Modern diagnosis of endometriosis state of the art. J Reproduct Med 33, 11:861 (1988)

67. Dmowski, W P: Endocrine properties and clinical application of danazol. Fertil Steril 31:237 (1979)

68. Buttram, V C, Reiter, R C, Ward, S: Treatment of endometriosis with danazol: report of a 6-year prospective study. Fertil Steril 43: 3 (1985)

72. Rose, G L, Dowsett, M, Mudge, J E, White, J O, Jeffcoate, S L: 266. The inhibitory effects of danazol, danazol metabolites, gestrinone and testosterone on the growth of human endometrial cells in vitro, item 73. Schriock, E, Monroe, S E, Henzl, M, Jaffe, R B: Treatment of endometriosis with a potent agonist of gonadotropin-releasing hormone (nafarelin). Fertil and Steril 44:5 (1985)

74. Lemay, A, Maheux, R, Huot, C, Blanchet J, Faure, N: Efficacy of intranasal or subcutaneous luteinizing hormone-releasing hormone agonist inhibition of ovarian function in the treatment of endometriosis. Am J Obstet Gynecol 158:233 (1988)

75. Cortes-Prieto, J, Lledo, A, Avila, C, Cortes-Garcia, L, D'acunto, A, Luisi, M, Comaru-Schally, A M, Schally, A V: Long-acting agonists of LH-RH in the treatment of large ovarian endometriomas. Int J Fertil 32, 4:290 (1987)

76. Gudmundsson, J A, Ljunghall, S, Bergquist, C, Wide, L, Nillius, S J: Increased bone turnover during gonadotropin relea-sing hormone superagonist-induced ovulation inhibition. J. Clin Endocrinol Metabol 65, 1: 159 (1987)

77. Steingold, K A, Cedars, M, Lu, J K H, Randle, D, Judd, H L, Meldrum D R: Treatment of endometriosis with a long-acting gonadotropin-releasing hormone agonist. Obstet Gynecol 69, 3:49 (1987)

The invention claimed is:

1. A method for the treatment of endometriosis or uterine fibroids in a human female patient who desires to maintain pregnancy, comprising administering to the patient in need thereof an effective amount of at least one mesoprogestin selected from the group consisting of J867, J912, and J956, wherein the daily dose of mesoprogestin is 0.5 to 50 mg, and wherein the treatment is effected with much reduced abortifacient activity compared to RU 486.

2. A method according to claim 1, wherein the method is for treating endometriosis.

3. The method of claim 1, wherein the daily dose of mesoprogestin is 5.0 to 50 mg.

4. The method of claim 2, wherein the daily dose of mesoprogestin is 5.0 to 50 mg.

5. The method of claim 1, wherein the daily dose of mesoprogestin is 10 to 25 mg.

6. The method of claim 2, wherein the daily dose of mesoprogestin is 10 to 25 mg.

7. The method of claim 1, wherein the mesoprogestin is J867.

8. The method of claim 2, wherein the mesoprogestin is J867.

9. The method of claim 1, wherein the mesoprogestin is J912.

10. The method of claim 2, wherein the mesoprogestin is J912.

11. The method of claim 1, wherein the mesoprogestin is J956.

12. The method of claim 2, wherein the mesoprogestin is J956.

13. The method of claim 1, wherein the method is for treating uterine fibroids.

14. The method of claim 3, wherein the method is for treating uterine fibroids.

15. The method of claim 5, wherein the method is for treating uterine fibroids.

16. The method of claim 13, wherein the mesoprogestin is J867.

17. The method of claim 14, wherein the mesoprogestin is J867.

18. The method of claim 15, wherein the mesoprogestin is J867.

19. The method of claim 1, wherein the at least one mesoprogestin is the sole active agent administered to the patient for the treatment.

20. The method of claim 3, wherein the at least one mesoprogestin is the sole active agent administered to the patient for the treatment.

21. The method of claim 13, wherein the at least one mesoprogestin is the sole active agent administered to the patient for the treatment.

22. The method of claim 1, wherein the treatment is effected without producing estrogen deficiency effects.

* * * * *